United States Patent [19]

Miles et al.

[11] 3,992,273

[45] Nov. 16, 1976

[54] METHOD OF PREPARING SUBSTITUTED PHENYL PHOSPHINIC ACIDS

[75] Inventors: James A. Miles, Olivette; Mark T. Beeny, St. Louis, both of Mo.

[73] Assignee: Monsanto Company, St. Louis, Mo.

[22] Filed: Oct. 9, 1975

[21] Appl. No.: 620,983

[52] U.S. Cl. .................................... 204/158 R
[51] Int. Cl.² ................................... B01J 1/10
[58] Field of Search ......................... 204/158 R

[56] References Cited

OTHER PUBLICATIONS

Obrycki et al., Jour. of Organic Chem., vol. 33 (1968) pp. 632–636.

*Primary Examiner*—Howard S. Williams
*Attorney, Agent, or Firm*—Richard H. Shear; Donald W. Peterson

[57] ABSTRACT

This invention relates to a method for preparing substituted phenyl phosphinic acids and derivatives thereof by photolysis of aryl iodides in the presence of alkyl phosphonites.

7 Claims, No Drawings

METHOD OF PREPARING SUBSTITUTED PHENYL PHOSPHINIC ACIDS

This invention relates to a novel method for preparing substituted phenyl phosphinic acids and derivatives thereof. More particularly, the present invention provides a novel method for preparing esters having the formula

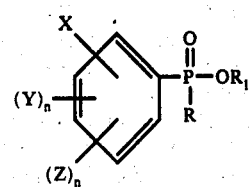

wherein R is selected from the group consisting of primary and secondary alkyl; $R_1$ is primary alkyl; X, Y and Z are independently selected from the group consisting of hydroxy, halo, trihalomethyl, primary and secondary alkyl, lower alkoxy and thioalkyl; and each $n$ is independently zero or one.

By the term "lower alkoxy" is meant those alkoxy groups which contain from one to three carbon atoms, inclusive.

Previous attempts to prepare substituted phenyl phosphinic acid derivatives of the foregoing formula have not been altogether successful. For example, synthesis of a large number of substituted phenyl phosphinic acids and derivatives thereof by the Friedel-Crafts reaction via aryl-dichlorophosphines is restricted due to the inherent limitations of the Friedel-Crafts reaction. The presence of ring-deactivating substituents precludes reaction between phosphorus trichloride and the ring. Reaction in the presence of ring-activating groups is limited to positions para to the activating group. Attempts to circumvent these restrictions have only been partially successful. Reaction of aryl Grignard reagents with bis-(N,N-diethyl-amino)-chlorophosphine has been used in preparing certain selected aryldichlorophosphines not available by the Friedel-Crafts reaction. In other cases, however, reaction of aryl Grignard reagents with a variety of tervalent phosphorus compounds have failed. It is, therefore, an object of the present invention to provide a method of preparing substituted phenyl phosphinic acids and their derivatives utilizing a more general, high yield procedure.

In accordance with the present invention, substituted phenyl phosphinic acid esters may be prepared by photolysis of aryl iodides in the presence of alkyl phosphonites. Generally, this reaction may be depicted as follows:

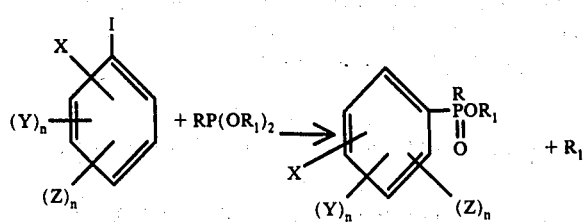

More particularly, phosphonic acid esters of Formula I may be prepared in accordance with the procedure of the following examples. Example 1 is illustrative of the general procedure which may be utilized to prepare the phosphinic acid esters. Examples 2-14 describe the preparation of specific compounds. These examples, however, are presented merely to illustrate the invention and are not meant as limitations thereof.

EXAMPLE 1

A quartz immersion well equipped with a water jacket for cooling and a high pressure mercury lamp, e.g. 450 watt mercury lamp, is placed within a reaction chamber to which is added the requisite aryl iodide and alkyl phosphonite. An inert atmosphere, e.g. nitrogen, is provided to exclude oxygen from the reaction chamber. Preferably, the reaction vessel is wrapped in aluminum foil. The lamp is illuminated for a period of time to effect complete reaction. A steady water supply is maintained through the immersion well such that the solution temperature remains between about 10° to 40° C. Preferably, the temperature ranges from 15° to 25° C. At the end of the reaction, the solution is vacuum distilled through a vigreux column to give the desired ester.

In a preferred embodiment of the invention, the molar ratio of the aryl iodide to the alkyl phosphonite ranges from 1:3 to 1:5. In other words, from 3 to 5 molar equivalents of phosphonite is used per mole of aryl iodide. Furthermore, the use of a quartz immersion well is necessary to obtain complete conversion of the reactants.

The free acid may be formed by reaction of the above-obtained ester with concentrated alkali, e.g. sodium hydroxide, followed by treatment with a strong acid, e.g. hydrochloric acid.

Salts such as the ammonium salt and alkyl and aryl amine salts of the substituted phenyl phosphinic acids are obtained by dissolving the free acid in acetone and reacting said acid with the appropriate amine or ammonium hydroxide.

EXAMPLE 2

Preparation of 2,6-Dimethoxy Phenyl Methyl Phosphinic Acid, Ethyl Ester

To 10 grams of 2,6-dimethoxyiodobenzene is added 26 grams of diethylmethyl phosphonite. After irradiating with a 450 watt high pressure mercury lamp for approximately 2½ hours, the solution is concentrated under reduced pressure to 16 grams of a clear oil. Vacuum distillation yields a viscous oil having a boiling point between 120° and 137° C. at 0.05 mm. Hg.

Analysis: Calculated for C, 54.06; H, 6.97. Found C, 54.05; H, 6.98.

EXAMPLE 3

Preparation of o-Hydroxy Phenyl Methyl Phosphinic Acid, Ethyl Ester

Using a 450 watt high pressure mercury lamp, 25 grams of o-iodophenol and 60 grams of diethylmethyl phosphonite are irradiated for approximately 3 hours. After concentrating the reaction mixture under reduced pressure and vacuum distilling, 14.5 grams of a product having a melting point between 117°–120° C. is yielded at 0.05–0.1 mm. Hg.

Analysis: Calculated for C, 54.00; H, 6.50. Found C, 53.85; H, 6.59.

EXAMPLE 4

Preparation of o-Trifluoromethyl Phenyl Methyl Phosphinic Acid, Ethyl Ester

Using a high pressure 450 watt mercury lamp, 13.6 grams of o-iodobenzotrifluoride and 25 grams of diethylmethyl phosphonite are irradiated in a small quartz cell. Vacuum distillation yields 10.8 grams of a product having a boiling point of 90° to 92° C. at 0.05 mm. Hg.

Analysis: Calculated for C, 47.6; H, 4.76. Found C, 47.64; H, 4.79.

EXAMPLE 5

Preparation of m-Fluorophenyl Methyl Phosphinic Acid, Ethyl Ester

Using a 450 watt high pressure mercury lamp, 23 grams of m-iodofluorobenzene and 60 grams of diethylmethyl phosphonite are irradiated in a 100 ml. pyrex jacket with a quartz immersion well. After concentration and vacuum distillation, 6 grams of a product having a boiling point of 98°–102° C. at 0.05 mm. is found along with 11 grams of a second fraction having a boiling point of 90°–98° C. at 0.05 mm. Hg.

Analysis: Calculated for C, 53.4; H, 5.94. Found C, 52.53; H, 6.28.

EXAMPLE 6

Preparation of o-Thiomethyl Phenyl Methyl Phosphinic Acid, Ethyl Ester

Using a 450 watt high pressure mercury lamp, 5 grams of o-iodothioanisole and 8.2 grams of diethylmethyl phosphonite are combined and irradiated for approximately 2 hours and 15 minutes. After concentration and vacuum distillation, 3.5 grams of a clear viscous oil having a boiling point of 121°–125° C. at 0.07 mm. Hg. is found.

EXAMPLE 7

Preparation of 2,5-Dichloro Phenyl Methyl Phosphinic Acid, Ethyl Ester

Using a high pressure 450 watt mercury lamp, 20 grams of 2,5-dichloroiodobenzene and 30 grams of diethylmethylphosphonite are combined and irradiated for approximately 3½ hours. After concentration and distillation, a clear oil is obtained, which then solidified. The solid is recrystallized from ethyl ether to give 8.5 g. of white needles having a melting point between 90° and 91° C.

Analysis: Calculated for C, 42.7; H, 4.35; Cl, 28.1. Found C, 42.72; H, 4.39; Cl, 27.97.

EXAMPLE 8

Preparation of o-Methyl Phenyl Methyl Phosphinic Acid

A solution of 73.0 grams of o-iodo toluene in 150 ml. of diethylmethylphosphonite is irradiated for 6 hours. The volatile material, having a boiling point below 50° C. at 0.1 mm. Hg., is distilled off the solution and the product remaining is distilled. After redistillation, 57.6 grams of the ester is obtained (b.p. 90°–95° at 0.15 mm. Hg.). The entire quantity of the ester is then combined with 60 ml. of a 50% aqueous sodium hydroxide solution and heated on a steam bath for 2 hours with intermittent stirring. The mixture is then diluted with 100 ml. of water and acidified with 12 M HCl. The acidified mixture is extracted with chloroform and the combined extracts are washed with water and dried over MgSO$_4$. Concentration under reduced pressure yields 40.1 grams of the phosphinic acid, m.p. 97°–98°.

EXAMPLE 9

Preparation of m-Hydroxyphenylmethyl Phosphinic Acid

After dissolving 4.4 grams of m-iodophenol in 10 ml. of diethyl methylphosphonite, the solution is irradiated for 5 hours. The solution is concentrated under reduced pressure and the resulting solution is distilled under vacuum to remove all material boiling below 45° C. at 0.1 mm. The pot residue consists primarily of the desired phosphinate ester. The ester is combined with 10 ml. of 50% sodium hydroxide solution and heated on a steam bath for 1 hour. The cooled mixture is diluted with 40 ml. of water and acidified with 12 M HCl. The acidified material is evaporated to dryness under reduced pressure and the resulting solid is extracted with acetone. The acetone solution is dried over MgSO$_4$, filtered and concentrated to leave a highly viscous oil which does not crystallize.

EXAMPLE 10

Preparation of m-Anisyl Methyl Phosphinic Acid Ammonium Salt

After dissolving 4.7 grams of m-iodoanisole in 10 ml. of diethyl methylphosphonite, the solution is irradiated for 5 hours. The solution is concentrated under reduced pressure and the product is distilled to give the desired phosphinic ester. The ester is combined with 6 ml. of 50% sodium hydroxide solution and heated on the steam bath for 1 hour. After diluting with 40 ml. of water and acidifying with 12M HCl, the aqueous mixture is evaporated to dryness under reduced pressure and the resulting solid is extracted with acetone. The acetone solution is dried over MgSO$_4$, filtered and concentrated to give 2.4 grams of a thick oil, the free acid. The oil is dissolved in acetone and concentrated ammonium hydroxide is added dropwise until precipitation ceases. The solid is collected, yielding 1.5 grams of the ammonium salt. Recrystallization from methanol-acetone yields a white crystalline product having a melting point of from 162°–172° C. (with decomposition).

Analysis: Calculated for C, 47.29; H, 6.95; N, 6.89. Found C, 47.21; H, 6.99; N, 6.90.

EXAMPLE 11

Preparation of o-Anisyl Hexyl Phosphinic Acid, Ethyl Ester

After dissolving 4.0 grams of o-iodoanisole in 9.2 grams of diethyl hexylphosphonite, the solution is irradiated for 5 hours. Distillation under vacuum yields 4 fractions having boiling points ranging from 30° to 134° C. (0.05–0.1 mm. Hg.). The last fraction, upon redistillation, yields three fractions having boiling points from 90° to 130° C., (0.05–0.1 mm. Hg.), the latter two fractions being the desired ester.

EXAMPLE 12

Preparation of o-Chlorophenyl Methyl Phosphinic Acid

After dissolving 4.8 grams of o-iodochlorobenzene in 10 ml. of diethyl methylphosphonite, the resulting solution is irradiated for 3 hours. After concentration under reduced pressure and vacuum distillation, a colorless oil is produced having a boiling point from 96°–100° C. (0.05–0.1 mm. Hg.). The product is combined with 25 ml. of 12M HCl, and the mixture is refluxed for 2 hours. The solution is concentrated to leave a thick oil which crystallizes upon trituration with ether. Upon recrystallization from acetone-ether, 0.5 grams of the solid is collected having a melting point of 97°–98° C.

EXAMPLE 13

Preparation of o-Methylphenyl Methyl Phosphinic Acid, Ethyl Ester

After dissolving 10.9 grams of o-iodotoluene in 25 ml. of diethyl methylphosphonite, the solution is irradiated for 3 hours. Concentration under reduced pressure and distillation under vacuum produces 7.6 grams of the ethyl ester having a boiling point from 91°–95° C. at 0.15 mm. Hg.

EXAMPLE 14

Preparation of o-Anisyl Isopropyl Phosphinic Acid

After dissolving 11.7 grams of o-iodoanisole in 28 ml. of diethyl isopropyl phosphonite, the solution is irradiated for 7 hours. After distillation under vacuum, the low boiling fractions are discarded. The product is then collected in two fractions, the first having a boiling point of from 101°–106° C. at 0.1 mm. Hg., and the second having a boiling point from 106°–108° C. at 0.1 mm. Hg. 7.7 grams of the ester is thus obtained. 2.2 grams of the ester is combined with 5 ml. of 50% sodium hydroxide solution and heated with stirring at reflux for 1 hour. The mixture is then diluted with 50 ml. of water and stirred until all the solid is dissolved. The basic aqueous solution is washed twice with chloroform, the organic washes being discarded. The aqueous solution is then acidified with 12M HCl, whereupon the product is precipitated. 0.9 grams of the product is collected and recrystallized from acetone, yielding 0.6 grams of the free acid having a melting point of from 156°–158° C.

The phosphinic acid esters and their derivatives as defined by the foregoing Formula I are useful as herbicides, particularly as controlling broadleaf weeds. Herbicidal use of said phosphinic acids and their derivatives is the subject of copending application Ser. No. 620,982, filed Oct. 9, 1975, by M. J. Sabacky.

While this invention has been described with respect to certain embodiments, it is to be understood that it is not so limited and that variations and modifications thereof obvious to those skilled in the art to which this invention appertains can be made without departing from the spirit or scope thereof.

What is claimed is:

1. A method for preparing substituted phenyl phosphinic acid esters having the formula

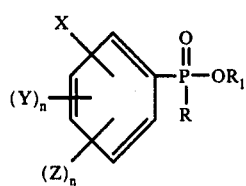

wherein R is selected from the group consisting of primary and secondary alkyl; $R_1$ is primary alkyl; X, Y and Z are independently selected from the group consisting of hydroxy, halo, trihalomethyl, primary and secondary alkyl, lower alkoxy and thioalkyl; and each $n$ is independently zero or one comprising the steps of adding an aryl iodide having the formula

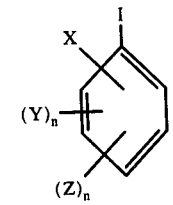

wherein X, Y and Z are defined as above to a lower alkyl phosphonite having the formula $RP(OR_1)_2$ wherein R and $R_1$ are defined as above to form a reaction mixture and irradiating said reaction mixture to form said substituted phenyl phosphinic acid ester.

2. A method according to claim 1 wherein said reaction mixture is placed under an inert atmosphere.

3. A method according to claim 1 wherein the molar ratio or aryl iodide to lower alkyl phosphonite within said reaction mixture ranges from 1:3 to 1:5.

4. A method according to claim 1 wherein said reaction mixture is irradiated with a high pressure mercury lamp.

5. A method for preparing substituted phenyl phosphinic acid esters by the formula

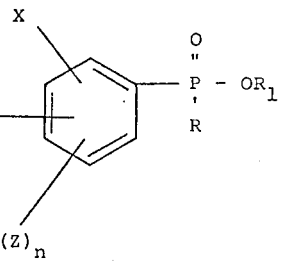

wherein R is selected from the group consisting of primary and secondary alkyl; $R_1$ is primary alkyl; X, Y and Z are independently selected from the group consisting of hydroxy, halo, trihalomethyl, primary and secondary alkyl, lower alkoxy and thioalkyl; and each $n$ is independently zero or one comprising mixing an aryl iodide having the formula

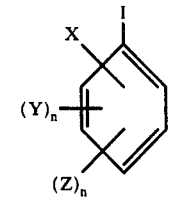

wherein X, Y and Z are defined as above and a lower alkyl phosphonite having the formula $RP(OR_1)_2$ wherein R and $R_1$ are defined as above in a reaction chamber for form a reaction mixture, placing a quartz immersion well equipped with a high pressure mercury lamp within said chamber and irradiating said reaction mixture to form said substituted phenyl phosphinic acid ester.

6. A method according to claim 5 wherein said reaction mixture is placed under an inert atmosphere.

7. A method according to claim 5 wherein the molar ratio of aryl iodide to lower alkyl phosphonite within said reaction mixture ranges from 1:3 to 1:5.

* * * * *